(12) United States Patent
Belei et al.

(10) Patent No.: US 12,167,929 B2
(45) Date of Patent: *Dec. 17, 2024

(54) ORIENTATION REFERENCE SYSTEM FOR MEDICAL IMAGING

(71) Applicant: KONINKLIJKE PHILIPS N.V., Eindhoven (NL)

(72) Inventors: Peter Belei, Hamburg (DE); Bart Carelsen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/241,346

(22) Filed: Sep. 1, 2023

(65) Prior Publication Data

US 2023/0404517 A1 Dec. 21, 2023

Related U.S. Application Data

(63) Continuation of application No. 16/262,478, filed on Jan. 30, 2019, now Pat. No. 11,771,395, which is a
(Continued)

(30) Foreign Application Priority Data

May 13, 2011 (EP) .................................... 11166065

(51) Int. Cl.
*A61B 6/58* (2024.01)
*A61B 6/00* (2024.01)
(Continued)

(52) U.S. Cl.
CPC ............ *A61B 6/589* (2013.01); *A61B 6/0487* (2020.08); *A61B 6/4441* (2013.01);
(Continued)

(58) Field of Classification Search
CPC ..... A61B 6/589; A61B 6/0487; A61B 6/4441; A61B 6/4464; A61B 6/461; A61B 6/467; A61B 6/4423; A61B 8/4444; A61B 8/461
See application file for complete search history.

(56) References Cited

U.S. PATENT DOCUMENTS 5,142,559 A    8/1992  Wielopolski et al.
5,189,690 A *  2/1993  Samuel ............. A61B 17/1703
                                                    378/162

(Continued)

FOREIGN PATENT DOCUMENTS

EP    1800593    6/2007
EP    1857051    11/2011
(Continued)

OTHER PUBLICATIONS

Visible. Merriam-Webster.com Merriam-Webster, n.d. Web. May 10, 2016.

*Primary Examiner* — David A Vanore (57) ABSTRACT

The present invention relates to positioning a medical imaging system in relation to an object. In order to provide improved positioning possibilities which facilitate the workflow during an intervention, a medical imaging apparatus (10) is provided with an image acquisition arrangement (12), which is positionable in relation to an object (16) to acquire image data (18) of the object from different directions. An output unit (14) is arranged to provide the image data. According to the invention, first movement direction indicators (22) are provided to indicate possible movement directions of the image acquisition arrangement in relation to the object. Further, a display apparatus (24), comprising a display area (26) to display image data (30) of an object provided by an image acquisition arrangement and a movement direction indication (28), may be provided, wherein the movement direction indication is configured to provide (Continued)

second movement direction indicators (32) in relation to the displayed image data of the object to indicate possible movement directions of the image acquisition arrangement in relation to the object. The first movement direction indicators and the second movement direction indicators are equivalent.

17 Claims, 7 Drawing Sheets

Related U.S. Application Data continuation of application No. 14/116,151, filed as application No. PCT/IB2012/052259 on May 7, 2012, now Pat. No. 10,219,776.

(51) Int. Cl.
    *A61B 6/04*      (2006.01)
    *A61B 6/46*      (2024.01)
    *A61B 8/00*      (2006.01)

(52) U.S. Cl.
    CPC ............ *A61B 6/4464* (2013.01); *A61B 6/461* (2013.01); *A61B 6/467* (2013.01); *A61B 6/4423* (2013.01); *A61B 8/4444* (2013.01); *A61B 8/461* (2013.01)

(56) References Cited

U.S. PATENT DOCUMENTS

| | | | |
|---|---|---|---|
| 6,160,870 A | 12/2000 | Jacobson | |
| 6,354,737 B1 | 3/2002 | Hufe et al. | |
| 7,092,491 B2 | 8/2006 | Okoda | |
| 7,123,690 B1 | 10/2006 | Brown et al. | |
| 7,277,594 B2 | 10/2007 | Hofstetter et al. | |
| 10,219,776 B2 * | 3/2019 | Belei | A61B 6/0487 |
| 11,771,395 B2 * | 10/2023 | Belei | A61B 6/4441 |
| | | | 378/205 |
| 2003/0108154 A1 | 6/2003 | Schmitt | |
| 2005/0000133 A1 | 1/2005 | Russell | |
| 2005/0047549 A1 | 3/2005 | Okoda | |
| 2005/0157847 A1 | 7/2005 | Marn | |
| 2008/0025466 A1 | 1/2008 | Peterfy | |
| 2010/0010348 A1 | 1/2010 | Ialmann | |
| 2010/0091951 A1 | 4/2010 | Ngo | |
| 2011/0050403 A1 | 3/2011 | Liu | |
| 2014/0072105 A1 * | 3/2014 | Belei | A61B 6/461 |
| | | | 378/205 |
| 2014/0077079 A1 | 3/2014 | Hogue | |
| 2016/0313266 A1 | 10/2016 | Sugiyama | |
| 2019/0167225 A1 * | 6/2019 | Belei | A61B 6/4464 |
| 2023/0404517 A1 * | 12/2023 | Belei | A61B 6/4441 |

FOREIGN PATENT DOCUMENTS

| | | |
|---|---|---|
| JP | 2011067509 | 4/2011 |
| WO | 2008120121 | 10/2008 |

* cited by examiner

ORIENTATION REFERENCE SYSTEM FOR MEDICAL IMAGING

CROSS-REFERENCE TO RELATED APPLICATIONS

This application is a continuation application of U.S. application Ser. No. 16/262,478, filed on Jan. 30, 2019, which is a continuation application of U.S. application Ser. No. 14/116,151 filed on Nov. 7, 2013, now issued as U.S. Pat. No. 10,219,776, which is a U.S. National Phase application under 35 U.S.C. § 371 of International Application No. PCT/IB2012/052259 filed May 7, 2012, which claims the benefit of European Patent Application No. 11166065.0 filed on May 13, 2011. These applications are hereby incorporated by reference herein.

FIELD OF THE INVENTION

The present invention relates to positioning a medical imaging system in relation to an object. In particular, the present invention relates to a medical imaging apparatus, a display apparatus for displaying medical image data of an object, an imaging system, and a method for positioning a medical imaging system.

BACKGROUND OF THE INVENTION

Medical imaging is commonly performed, for example, during operational procedures, such as in a hospital. To acquire image data of an object under investigation or examination from different directions, an image acquisition device can be moved in relation to the object. To provide a surgeon, for example, with image information about the current situation, for example during an interventional procedure, images are provided, for example, on a display. In case the surgeon requires image data from a different region of interest, or from a different direction, the image acquisition device and the object, for example a patient, are moved in relation to each other such that further images can be acquired from a different position. Usually, this is performed by an image acquisition operator. Thus, a respective instruction has to be communicated to the operator. However, instructions by the surgeon may be misleading, for example an instruction like "move upwards", which may refer to the displayed image as well as to the image acquisition device itself. Thus, it has been shown that after a further image acquisition step, still further adjustment instructions concerning the position of the image acquisition device in relation to the patient are quite often necessary. An imaging system is described in WO 2008/120121 A1, wherein an adjustment of the table in relation to the imaging unit is provided to maintain the region of interest within the image region of the imaging unit in response to a rotation of the imaging unit about an axis of rotation, to assure that the region of interest is within the image area of after rotating the imaging unit.

SUMMARY OF THE INVENTION

There is a need to provide improved positioning possibilities which facilitate the workflow during an intervention.

The object of the present invention is solved by the subject-matter of the independent claims, wherein further embodiments are incorporated in the dependent claims.

It should be noted that the following described aspects of the invention apply also for the medical imaging apparatus, the display apparatus, the imaging system, and the method for positioning a medical image system.

According to a first aspect of the invention, a medical imaging apparatus is provided, comprising an image acquisition arrangement, and an output unit. The image acquisition arrangement is positionable in relation to an object to acquire image data of the object from different directions. For the positioning, the image acquisition arrangement is movable in relation to the object in at least two movement directions. The output unit is arranged to provide the image data. First movement direction indicators are provided to indicate possible movement directions of the image acquisition arrangement in relation to the object.

In relation with the present invention, the term "direction" refers to movement possibilities, which movements comprise translations and rotations, i.e. translational and rotational movements, as well as combinations thereof. Thus, the term "movement direction indicator" refers to movement possibilities and can thus be understood as "movement possibilities indicator".

For example, the image acquisition arrangement is movable in relation to the object by translational movement. As another example, the image acquisition arrangement is movable in relation to the object by rotational movement. Still further, the image acquisition arrangement is movable in a combination of rotation and translation.

The rotational movement, the translational movement as well as the combinations thereof, can be provided in a plane as one- or two-dimensional movement. The rotational movement, the translational movement as well as the combinations thereof, can also be provided in space as three-dimensional movement.

According to an exemplary embodiment of the invention, the image acquisition arrangement is an X-ray imaging device with an X-ray source and an X-ray detector.

According to a further exemplary embodiment, the first movement direction indicators are provided on the image acquisition arrangement such that they are visible to the user.

According to a further exemplary embodiment, the first movement direction indicators are provided next to a control interface for accomplishing the positioning.

According to a further exemplary embodiment, the first movement direction indicators are provided such that a bijective identification of the complementary direction is possible.

According to a second aspect of the invention, a display apparatus for displaying medical image data of an object is provided, comprising a display area and a movement direction indication. The display area is configured to display image data of an object provided by an image acquisition arrangement. The movement direction indication is configured to provide second movement direction indicators in relation to the displayed image data of the object to indicate possible movement directions of the image acquisition arrangement in relation to the object.

According to a further exemplary embodiment, the movement direction indication is configured to be updated after a positioning movement.

According to a third aspect of the invention, an imaging system is provided, comprising a medical imaging apparatus according to one of the above described aspects and embodiments, and a display apparatus according to one of the above described aspects and embodiments. The output unit is configured to provide the image data to the display apparatus. The movement direction indication on the display apparatus relates to the movement possibilities of the image acquisition arrangement. The first movement direction indicators and the second movement direction indicators are equivalent.

According to a further exemplary embodiment, the first and the second movement direction indicators are of the same type.

According to a fourth aspect of the invention, a method for positioning a medical image system is provided, comprising the following steps: a) providing first movement direction indicators indicating possible movement directions of an image acquisition arrangement in relation to an object; b) displaying image data of the object, and providing second movement direction indicators in relation to a displayed image data of the object, which second movement direction indicators indicate the different movement directions of the image acquisition arrangement; wherein the first and the second movement direction indicators are equivalent; c) identifying at least one of the second movement direction indicators for an intended movement of the image acquisition arrangement; and d) accomplishing the intended movement of the image acquisition arrangement in relation to the object on behalf of at least one of the first movement direction indicators which is equivalent to the identified second movement direction indicator.

According to an aspect of the invention, for example, in case of an operational intervention, the surgeon is provided with direction indicators that can be used for instructing the required movements in case of a desired (re-) positioning or (re-) adjustment of the image acquisition device. Since, for the performance of the positioning or adjustment of the image acquisition device, equivalent direction indicators are provided, for example to the operator responsible for accomplishing the positioning procedure, it is possible to give clear and direct instructions which cannot be misinterpreted, but which rather result in a precise positioning for further image acquisition steps. According to an aspect of the invention, an orientation reference system is thus provided, which is presented on the one hand to the (first) user via providing movement direction indicators on the display, and on the other hand presented to a staff member (as second user) responsible for accomplishing the actual movement of the image acquisition device or arrangement, in form of further movement direction indicators, both of which indicator groups are equivalent to each other, thus forming an orientation reference system according to the invention. The inventive orientation reference system provides improved positioning possibilities facilitating the workflow during an intervention. In particular, in case of X-ray imaging, the orientation reference system saves unneeded, and thus unwanted, X-ray radiation procedures, thereby reducing the overall amount of radiation to which the patient is exposed to, due to the improved positioning and alignment commands provided by the equivalent movement direction indicators.

These and other aspects of the present invention will become apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
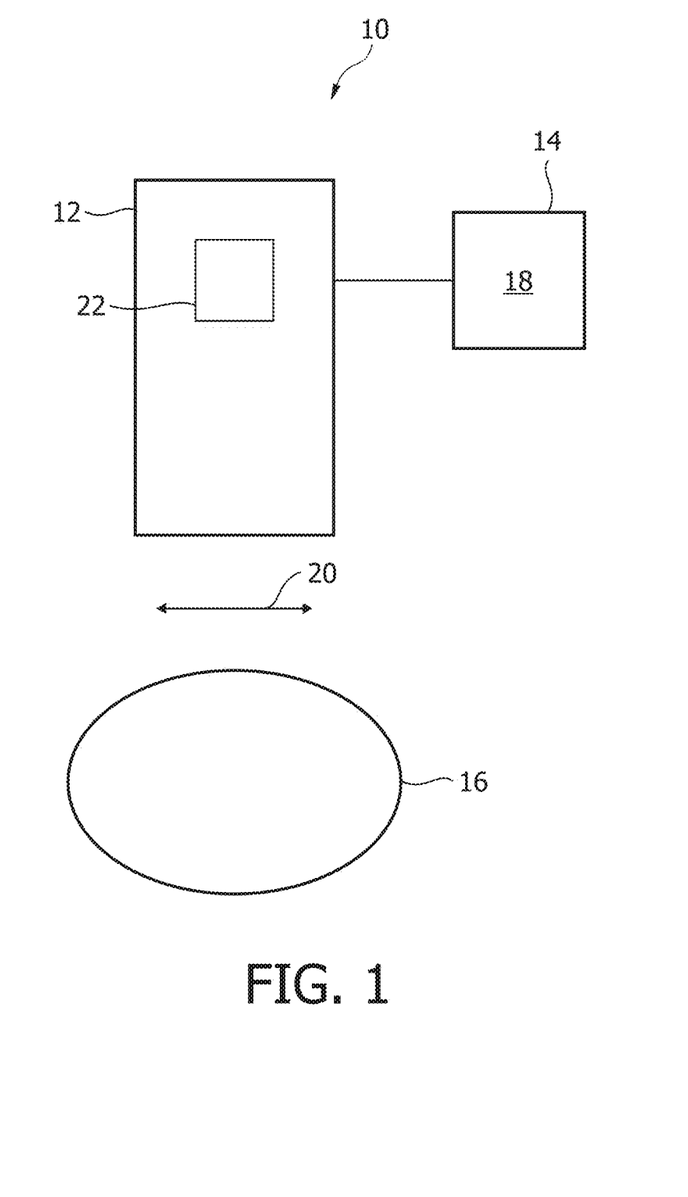
FIG. 1 illustrates a medical imaging apparatus according to an exemplary embodiment of the invention.

FIG. 1 shows a medical imaging apparatus 10 with an image acquisition arrangement 12 and an output unit 14. The image acquisition arrangement 12 is positionable in relation to an object 16 to acquire image data 18 of the object 16 from different directions. For example, the object 16 is a patient. For the positioning, the image acquisition arrangement 12 is movable in relation to the object in at least two movement directions, which is indicated by a double arrow 20. The output unit 14 is arranged to provide the image data 18.

According to the invention, first movement direction indicators 22 are provided to indicate possible movement directions of the image acquisition arrangement in relation to the object.

According to a further exemplary embodiment, although not further shown in FIG. 1, for the movement of the image acquisition arrangement in relation to the object, the image acquisition arrangement is movable.

The image acquisition arrangement may be movable by a direct interaction of the user or an operator, for example by manual actuation of the positioning. The movement can also be accomplished with the aid of mechanical movement devices or actuators, such as electro-magnetic or pneumatic driving devices.

The relative movement of the image acquisition arrangement in relation to the object can also be accomplished by a movement of the object itself, for example, with a moveable object support device, such as a movable patient table.

The relative movement can also be accomplished by both moving the image acquisition arrangement and the object itself.

According to the present invention, the first movement direction indicators, which will be discussed in more detail below, allow an identification of the different movement directions, and thus allow to address, as well as to perform, a movement of the image acquisition arrangement in relation to the object for the image acquisition of the object from different directions or different positions.

Figure 2:
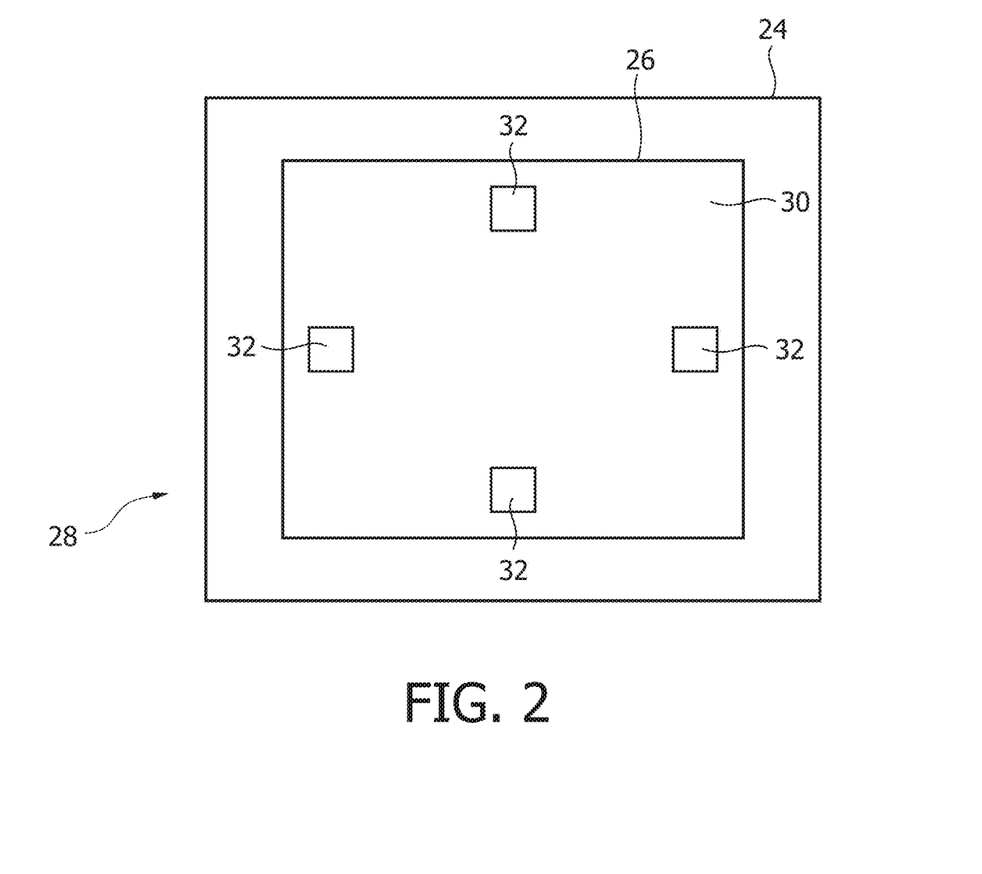
FIG. 2 illustrates a display apparatus according to an exemplary embodiment of the invention.

FIG. 2 shows a display apparatus 24 for displaying medical image data of an object. The display apparatus 24 comprises a display area 26 and a movement direction indication 28. The display area 26 is configured to display image data 30 of an object, for example a patient, provided by an image acquisition arrangement.

The term "image data" refers to directly detected image data as well as to processed image data. For example, image as detected is shown on the display. The detected information may also be transformed by image processing steps, such as digital subtraction steps, e.g. based on previously acquired image data. The detected information may also be transformed or processed into further image information such as a generated model, a segmented structure or the like.

The movement direction indication 28 is configured to provide second movement direction indicators 32 in relation to the displayed image data of the object to indicate possible movement directions of the image acquisition arrangement in relation to the object. For example, four second movement direction indicators 32 are shown. Of course, other numbers of the first and second movement direction indicators are also possible.

For example, the movement direction indication is configured to provide the second movement direction indicators 32 according to the correlation of the orientation of the displayed image to the orientation of a detector of the image acquisition arrangement.

According to a further aspect of the invention, the second movement direction indicators on the display apparatus correlate with the movement directions of the image acquisition arrangement in correlation with the image plane of the displayed image.

The first movement direction indicators 22 and the second movement direction indicators 32 will also be explained in the following.

Figure 3:
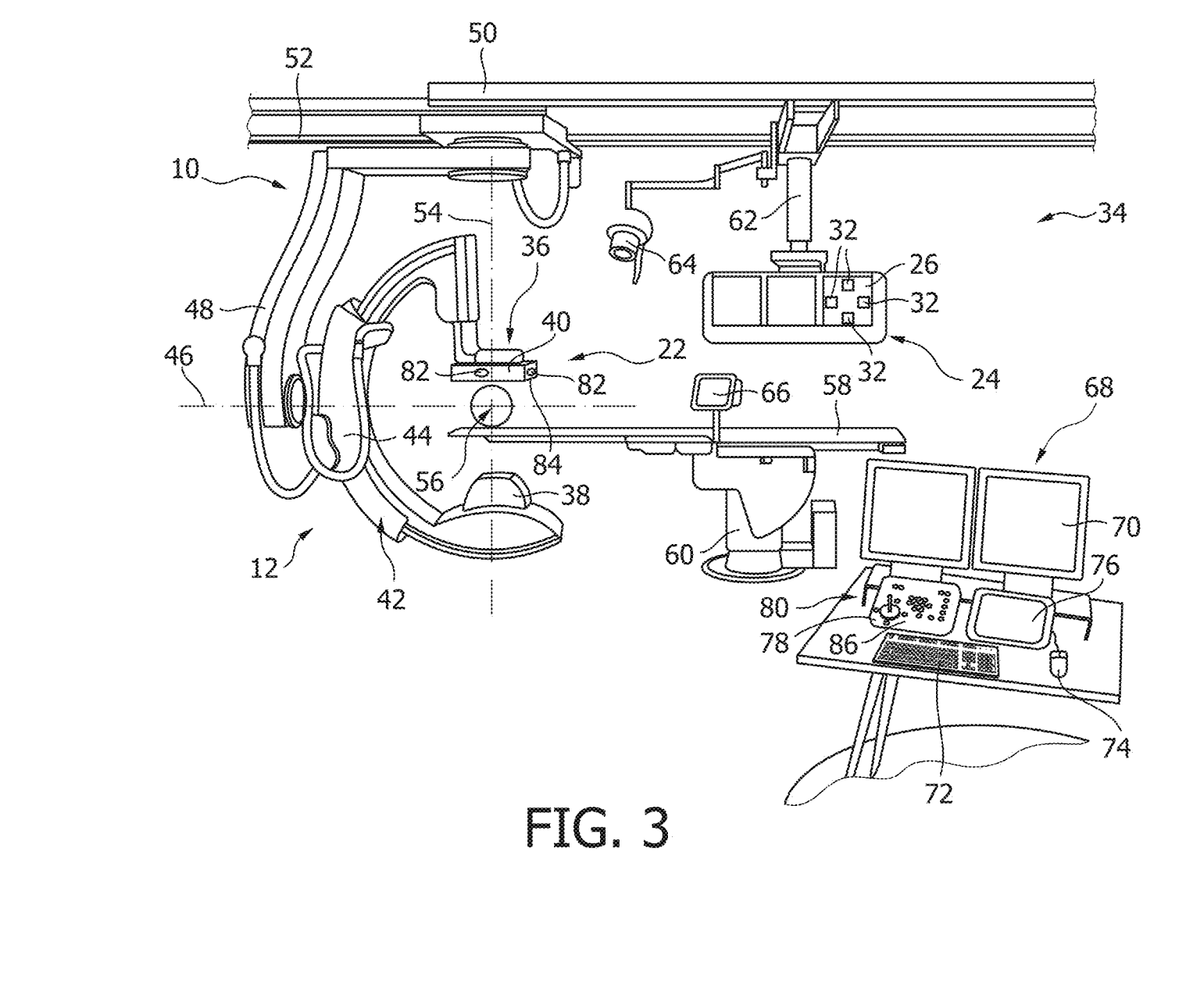
FIG. 3 illustrates an imaging system according to an exemplary embodiment of the invention.

FIG. 3 shows an imaging system 34 with a medical imaging apparatus 10 and a display apparatus 24, which have already been described in basic aspects above.

As an example for a medical imaging apparatus 10, the image acquisition arrangement 12 is an X-ray imaging device 36 with an X-ray source 38 and an X-ray detector 40. For example, the X-ray imaging system device 36 may be a C-arm device, as shown for exemplary purposes in FIG. 3. The C-arm device as shown, for example, may comprise a C-arm structure 42, to which both ends the detector 40 and the X-ray source 38 are mounted. The C-arm structure 42 is movably mounted to a support 44, in which the C-arm is slideably mounted. The support 44 also allows rotational movement around a horizontal axis 46. The support 44 is mounted to a suspended arm structure 48 with an L-shape, shown only for exemplary purposes. The L-arm structure 48 is mounted to a support 50, which is mounted to the ceiling of the operational theatre and allows a horizontal movement along support rails 52 as well as a rotational movement around a vertical axis 54.

The C-arm device is provided such that an object 56 can be located between the detector 40 and the X-ray source 38, in a way that, due to the different moving possibilities of the C-arm, image acquisition of the object 56 is possible from a number of different directions, which are not further shown.

The object 56 is arranged on a support device, for example a patient table 58, allowing horizontal and vertical adjustment for further positioning and adjustment purposes. Therefore, the table 58 is supported by a respective adaptable stand 60.

The display apparatus 24 is provided in the vicinity of the patient table, for example by being mounted to a ceiling support 62, which allows position adjustment of the display apparatus 24, according to the user's needs.

Further, adaptable lighting 64 is indicated, as well as an input or control interface 66 for adjusting peripheral equipment, such as the lighting 64 or the table 58.

Further, a control arrangement 68 is shown in the foreground, which comprises a plurality of display devices 70, as well as a plurality of input devices, for example a keyboard 72, a mouse 74, a graphic tablet 76, as well as an input device 78 with a joystick 80.

The control interface 78 may be provided for accomplishing a positioning of the medical imaging apparatus, for example the C-arm device. For example, the movement of the C-arm may be actuated and controlled by the joystick, with which positioning commands can be entered to control the medical imaging apparatus.

The first movement direction indicators 22 are provided on the image acquisition arrangement such that they are visible to the user. For example, the first movement direction indicators are arranged on visible housing parts, such as the housing of the detector, or support parts of the image acquisition arrangement, wherein the housing or support parts are moving in accordance with the position movement. As an example, reference numerals 82 indicate first movement direction indicators 22 provided on the surrounding faces of the housing of the detector 40. Thus, the first movement direction indicators 22 identify possible movement directions of the image acquisition arrangement.

The first movement direction indicators may be referred to as an orientation system of the image acquisition arrangement.

Figure 8A:
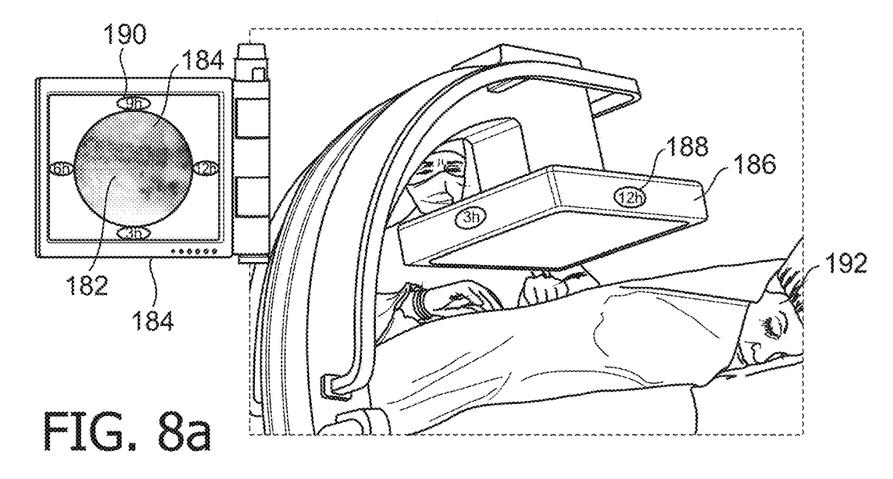
FIGS. 8A to 8C illustrate further aspects of the present invention.
Figure 8B:
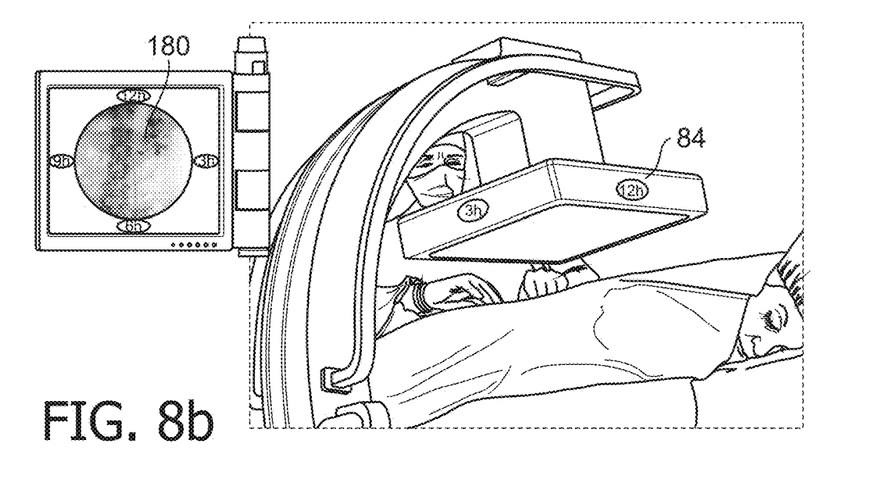
Figure 8C:
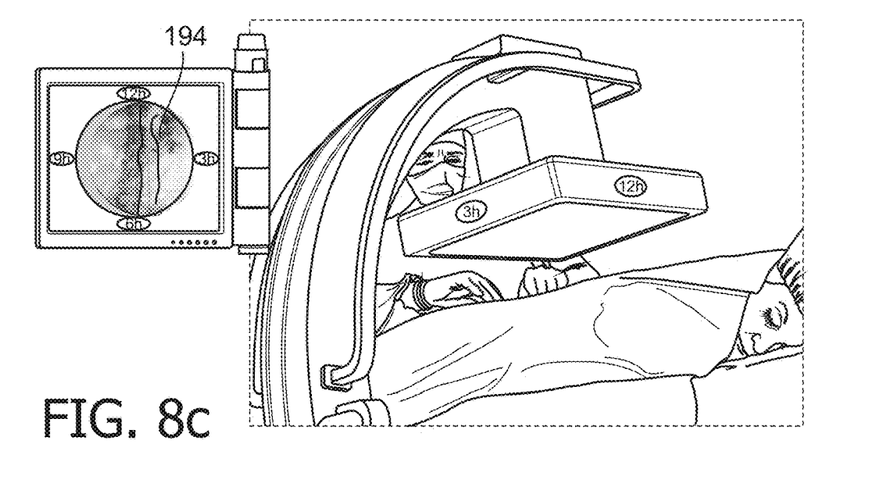

According to a further exemplary embodiment of the invention, the first movement direction indicators 22, 82 are provided as adaptable movement direction indicators 84, as is also shown in relation with FIG. 8. For example, the first movement direction indicators may be provided as one or more display units with adjustable display content. This allows, for example, adjusting the displayed content, i.e. the adjustment of the first movement direction indicators according to different needs and individual situations.

In case the first movement direction indicators are adapted or changed, the second movement direction indicators may be adapted or changed accordingly.

Of course, theoretically, the first and second movement direction indicators could be different, but this would mean the necessity of a decoding or translation step on the side of at least one of the users, which could then lead to unwanted misunderstanding.

For example, the adaptable first movement direction indicators 84 may be provided as bi-stable displays. These displays only need electric supply for their activation and change of the display content, respectively. That is, once they have been adjusted to show or display the desired information, the electric supply can be disconnected.

As already mentioned in relation with FIG. 2, the display apparatus 24 comprises the display area 26 to display the image data 30 of the object 56, which image data 30 is provided by the image acquisition arrangement 10.

For example, the second movement direction indicators 32 are shown in the edge zone of the display area 26, for example, overlaid to the displayed image data 30.

As an aspect of the invention, the first movement direction indicators 22 and the second movement direction indicators 32 are equivalent.

The term "equivalent" refers to the first and second movement direction indicators being synonymic, or being in a predetermined reference to each other, or being comparable. Thus, the term "equivalent" refers to the first and the second movement direction indicators as being corresponding to each other.

According to an exemplary embodiment of the invention (not further shown), the first and the second movement direction indicators are of the same type.

According to an exemplary embodiment of the invention (not further shown), the first and the second movement direction indicators can have different members, but with the same sort or type of symbols and the same logic.

By providing the medical imaging apparatus and the display apparatus with a common orientation reference system in form of the first and second movement direction indicators, it is possible that a surgeon, for example, studying the displayed image of the object, for example of a patient, finds movement direction indicators next to the image such that he or she can identify a desired movement direction of the image acquisition arrangement in relation to the object for further acquisition steps. Thus, for determining the further necessary movement of the apparatus in relation with the patient, these directions can correctly be addressed, which means relieve with respect to the user's time and attention needed to identify the movement direction.

Once the surgeon has identified the desired movement direction, the repositioning or adjustment of the position of the image acquisition apparatus can easily be accomplished by a staff member responsible for operating the device, for example a technician. For example, in case of a direct manual actuation of the positioning, i.e. by direct interaction with the C-arm itself, the technical operator finds the equivalent movement direction indicator on the housing of the detector, for example, such that he or she directly knows in which direction the image acquisition arrangement has to be moved for further acquisition steps.

Showing the orientation information on the device and on the display is also helpful for the surgeon to move the C-arm in the right direction himself.

By providing the first movement direction indicators next to the control interface 78, for example next to the joystick 80, as indicated with small dots 86, it is also possible to enter a respective control command by the joystick 78 by simply receiving the respective movement command in form of the second movement direction indicator, and to look for the equivalent first movement direction indicator next to the joystick 78.

Of course, the first movement direction indicators 22 could also be provided on the monitor or displays 70, the graphic tablet 76, or also in relation with the mouse 74 or the keyboard 72.

The first and second movement direction indicators will further be explained in relation with FIGS. 6A to 6E.

Figure 4:
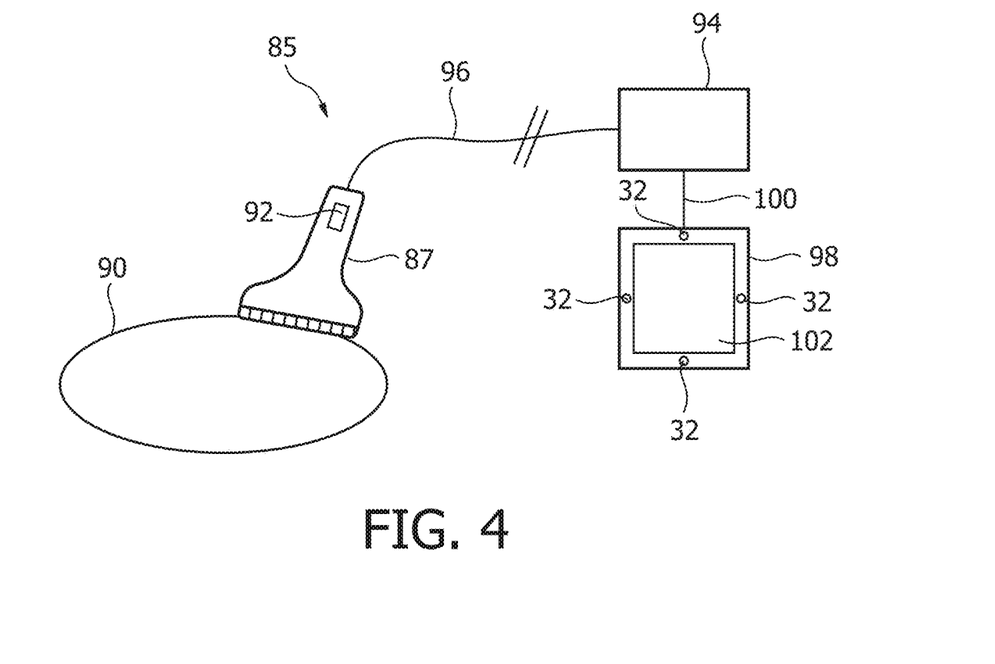
FIG. 4 illustrates a further exemplary embodiment of a medical imaging apparatus.

Before explaining the movement direction indicators, it is referred to FIG. 4, showing an ultrasound device 85 as a further example for an image acquisition arrangement. The ultrasound device 85 has a movable transducer unit 87 to be moved along an object 90, for example a patient, wherein the first movement direction indicators are provided on the outside of the transducer unit 87 as indicated with reference numeral 92. As further shown, the ultrasound device 85 may be connected to a processing unit 94, for example by a wire connection, which could also be provided as a wireless connection. Further, a display 98 can be connected to the processing unit 94, as schematically indicated with a connection line 100. The display 96 provides the second movement direction indicators 32, for example in the surrounding of a displayed ultrasound image 102. Of course, the second movement direction indicators 32 could also be provided as overlay to the ultrasound image 102. This allows to identify a movement direction by looking at the ultrasound image 102 and then to identify the necessary movement of the, for example, handheld movable transducer unit 87 by looking for the equivalent of the first movement direction indicators 92. It is also possible to have one person conducting the movement of the transducer unit 87, and another person studying the ultrasound image 102, to identify the necessary movements which will then be conducted by the first person.

Figure 5:
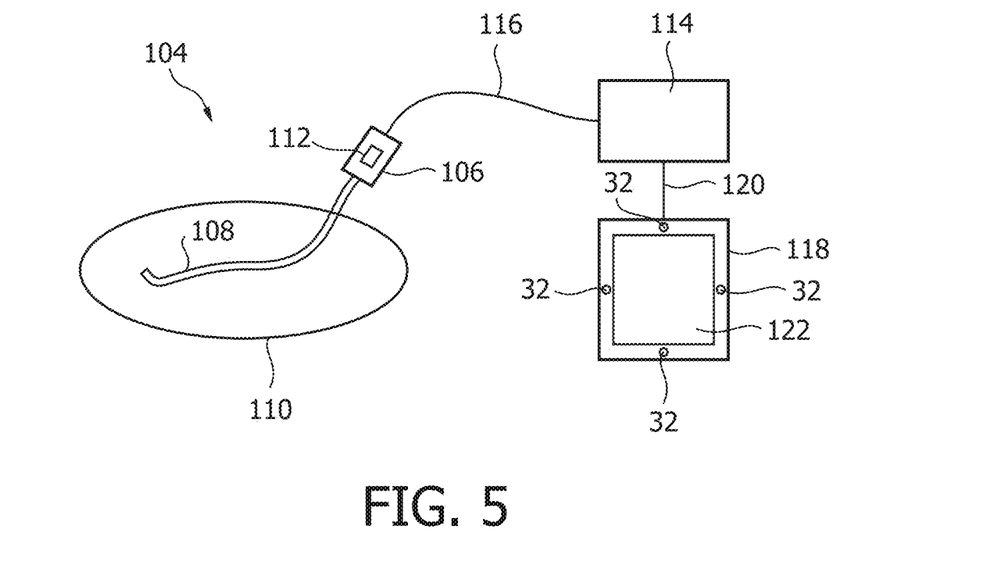
FIG. 5 shows a further exemplary embodiment of a medical imaging apparatus.

FIG. 5 shows a further example of an image acquisition arrangement in form of a steerable catheter device 104 with a handheld control device 106 to move and steer a catheter 108 inside an object structure 110, for example inside a patient's vessel structure or other tubular structure. First movement direction indicators, indicated with reference numeral 112, are provided on the outside of the control device 106 next to the control or regulation mechanism. The steerable catheter device may provide image data to a processing unit 114, connected to the catheter device by a wire connection or wireless connection 116, which processing unit 114 is further connected to a display 118 by a further connection 120. Second movement direction indicators 32 may be provided next to an image 122. Thus, the movement directions for next image acquisitions may be identified by looking at the display 118, which movement directions can then be identified on behalf of the equivalent first movement direction indicators 112 as provided on the handheld control device 106.

According to a further example (not shown), a stiff endoscope is provided, which, for example, can be used in arthroscopy or laparoscopy, in which similar first movement direction indicators are provided, as well as second movement direction indicators. The orientation, given by the movement direction indicators, facilitates, for example, the orientation for the user to move the endoscope in the desired direction.

According to an aspect of the present invention, the movement direction indicators are provided such that a bijective identification of the complementary direction is possible. In the context of the present invention, the complementary direction is the opposite direction, i.e. the same line in a plan or in space, but with an opposite orientation. This, and also the following passages, may apply for the first and/or the second movement direction indicators.

For example, the coding of the movement direction indicators is provided such that in case of partly hidden movement direction indicators, the non-visible movement direction indicators can be identified. For example, in such case where a surgeon is standing on one side of an image acquisition arrangement, being able to see only a part of the provided movement direction indicators, and an operator responsible for the positioning of the imaging apparatus is standing on the other side, where the part visible for the surgeon is not visible, but the part hidden for the surgeon is visible, both users can identify the respective movement direction indicator as seen from the other user.

According to a further aspect of the invention, the movement direction indicators are provided as denominated symbols such that the movement directions are addressable with unambiguous messages. The messages may be used in a communicatively way. For example, the messages may be terms such as spoken words, for example commands. The messages may also be gestures conducted by the surgeon. For example, the terms are common words to be called by both user identifying desired or intended movement direction and an operator initiating the movement, for example to confirm the respective movement command.

According to the present invention, the movement direction indicators relate to different movement directions such that opposing directions are indicated with different denominated symbols, clearly allowing an identification of the respective movement direction.

According to a further exemplary embodiment of the invention, the movement direction indicators are provided for a movement plane, wherein the movement direction indicators are provided as a planar orientation coding 150, as will be described with reference to FIGS. 6A to 6D.

Figure 6A:
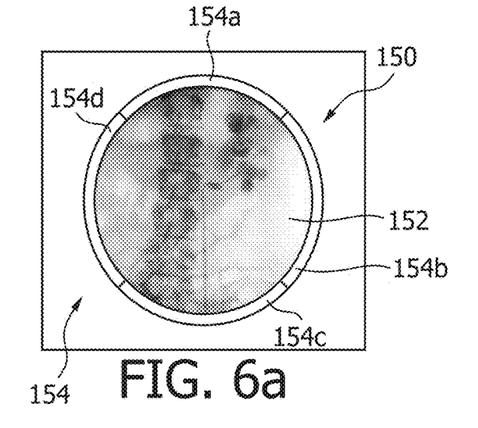
FIGS. 6A to 6E illustrate examples of movement direction indicators.

FIG. 6A shows a medical image, for example an X-ray image 152, in which, as second movement direction indicators, a surrounding chromatic circle 154 is shown with four different colours 154a, 154b, 154c, and 154d. For example, the four colours are arranged such that the respective opposite colour is provided as a complementary colour.

Figure 6B:
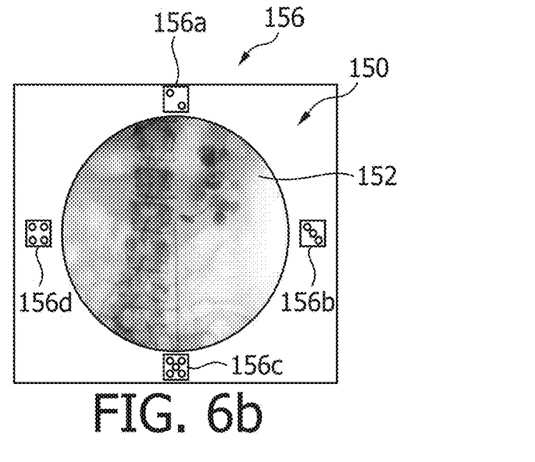

FIG. 6B shows the second movement direction indicators as dotted coding 156 with a first dot symbol 156a, a second dot symbol 156b, a third dot symbol 156c, and a fourth dot symbol 156d. The dot symbols are provided such that respective opposite symbols show the sum 7 in total. Thus, by only being able to see one part of the symbols, the respective opposite symbols can be identified.

Figure 6C:
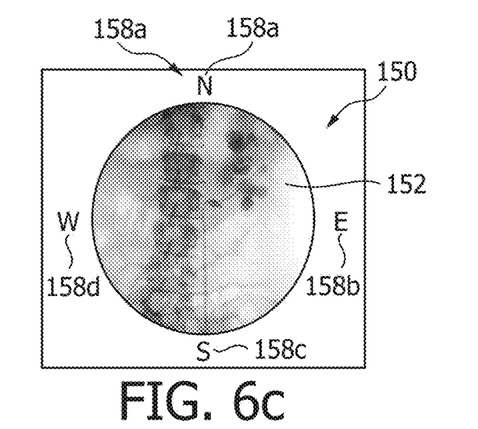

FIG. 6C shows a cardinal direction system 158 with a letter "N" as first cardinal direction indicator 158a, an "E" as second cardinal direction 158b, an "S" as third cardinal direction 158c, and a "W" as fourth cardinal direction 158d.

Figure 6D:
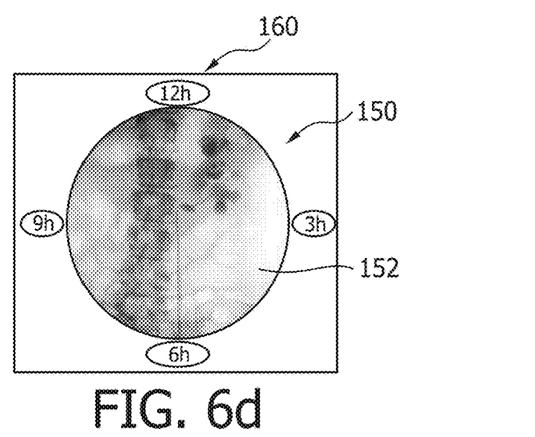

FIG. 6D shows clock positions 160 with the clock numbers "3", "6", "9", and "12" arranged around the X-ray image 152.

The movement direction indicators may also be provided relating to two-dimensional Cartesian coordinate system.

According to a further exemplary embodiment of the invention, the second (and first) movement direction indicators relate to a spatial movement in relation to an image plane, wherein the movement direction indicators are provided as a spatial orientation coding 162.

Figure 6E:
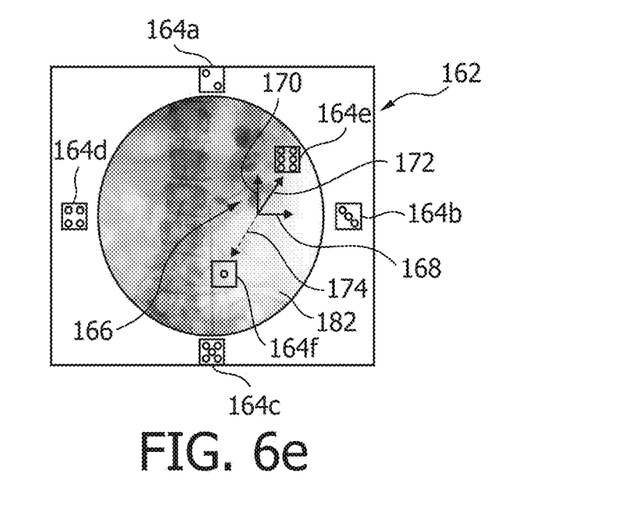

According to a further example, numerical indicators 164 of a virtual dice are shown wherein the dice has n faces. The numerical indicators are arranged such that the sum of opposing numerical indicators is n+1. As indicated in FIG. 6E, four numerical indicators 164a to 164d are arranged around the X-ray image 152. A fifth numerical indicator 164e and a sixth numerical indicator 164f are provided in combination with a three axis graph 166 indicating the plane of the image with a horizontal axis 168 and a vertical axis 170, and the direction in the depth of the image plane with a further third axis 172. The direction from the image plane towards the user, i.e. in the opposite direction than the depth direction 172, a still further arrow 174 is shown in a dotted manner. Thus, all directions of a dice with six faces are provided, wherein the respective opposing faces sum up to the number of seven to provide the possibility to identify the respective complementary direction.

The terms "up", "down", "right", "left", "depth" etc. relate to the image plane, and thus the detector plane and not to an actual position.

According to a further example, although not further shown, the spatial movement can also result in spatial orientation coding in form of a spherical colour model. For example, complementary colours are oriented on opposing sides of the spherical colour model.

The first and second movement direction indicators may be provided relating to a three-dimensional Cartesian coordinate system. The movement direction indicators may further be provided relating to a cylindrical or spherical coordinate system. The movement direction indicators may also be referred to as orientation symbols.

It is explicitly noted that the above described aspects in relation with the second movement direction indicators shown in the context of the displayed image, also apply for the first movement direction indicators as well. In particular, the first and second movement direction indicators are provided such that a bijective identification of the complementary direction is possible. The first and the second movement direction indicators thus correlate with the movement direction of the image acquisition apparatus.

As indicated above, according to an exemplary embodiment of the invention (not further shown), the display area may be configured to provide the second movement direction indicators in combination with the image data. For example, the second movement direction indicators may be provided superimposed at the edge areas of the display area. The display arrangement may also comprise an orientation area at the edge or outside of the display area in order to provide the movement direction indicators. Of course, the provision of an edge area outside of a display arrangement can also be provided in combination with overlaid indicators to an actually displayed image.

Figure 7:
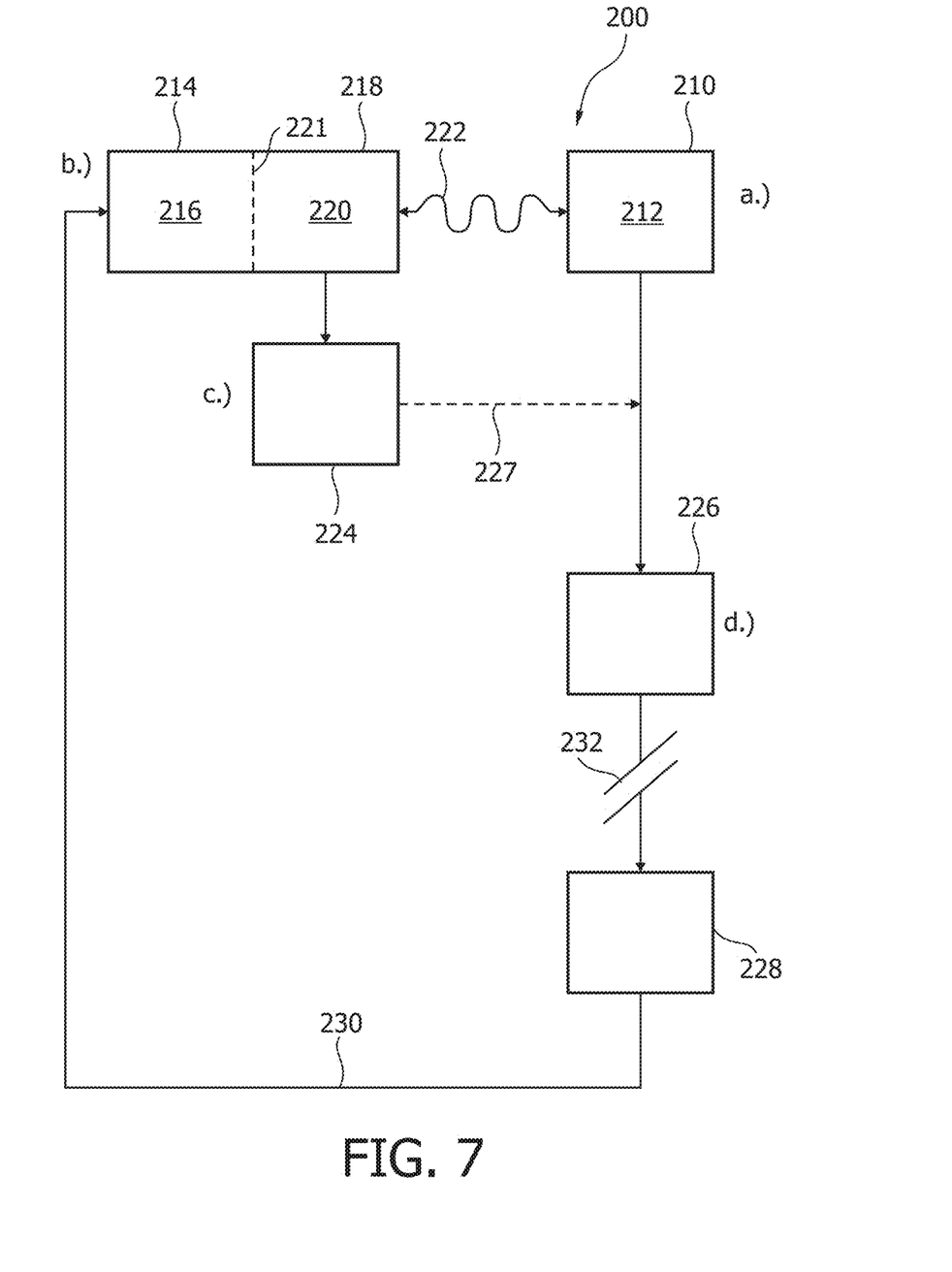
FIG. 7 illustrates basic steps of a method according to an exemplary embodiment of the invention.

In the following, basic steps of a method 200 shall be explained with reference to FIG. 7. In a provision step 210, first movement direction indicators 212 indicating possible movement directions of an image acquisition arrangement in relation to an object are provided. In a further step, a displaying sub-step 214 is provided in which image data 216 of the object is displayed. In a further provision sub-step 218, second movement direction indicators 220 are provided in relation to the displayed image data of the object, which second movement direction indicators indicate the different movement directions of the image acquisition arrangement. The displaying sub-step 214 and the provision sub-step 218 may also be provided as two parallel steps, which is also indicated with a dotted separation line 221.

According to the present invention, the first and the second movement direction indicators 212, 220 are equivalent to each other, which is indicated by a wave-like line with double arrows 222.

In an identification step 224, at least one of the second movement direction indicators 220 for an intended movement of the image acquisition arrangement is identified. Further, in an accomplishment step 226, the intended movement of the image acquisition arrangement in relation to the object is accomplished on behalf of at least one of the first movement direction indicators which is equivalent to the identified second movement direction indicator. Thus, the second movement direction indicator identified in the identification step 224 is so-to-speak transferred to the first movement direction indicators 212 to identify the respective equivalent, which is indicated by a dotted arrow 227.

The first provision step 220 may also be referred to as step a), the displaying and provision sub-steps 214, 218 may also be referred to as step b), the identification step 224 as step c), and the accomplishment step 226 as step d).

According to a further exemplary embodiment, the movement direction indication is configured to be updated after a positioning movement.

According to an example, not further shown, a movement of the medical imaging apparatus in relation with the object is detected and the respective information is provided to the display, where the second movement direction indicators are updated such that the actual position of the imaging apparatus in relation with the object is presented in form of the position of the second movement direction indicators in relation to the image of the object. For example, a C-arm is rotated in relation to the object for x degrees for positioning. Thus, a second indicator, on the display, showing a certain movement possibility of the C-arm is rotated respectively in relation to the image of the object on the display; i.e. in case the image is kept unchanged, the second indicator is rotated also for x degrees.

According to a further example, also not shown, a movement of the medical imaging apparatus in relation with the object is detected and the respective information is provided to the display. Further, a new image is acquired and the image data is provided on the display. The second movement direction indicators are updated such that the actual position of the imaging apparatus in relation with the object is presented in form of the position of the second movement direction indicators in relation to the (new) image of the object.

According to a further example, also not shown, a movement of the image in relation to the display can also be reflected in an update of the second movement direction indicators. For example, an image is rotated for 90 degrees for better understanding, leaving the C-arm at its position. The second movement direction indicators are also rotated, together with the image, for 90 degrees.

The update may be provided after a positioning movement and a further image data acquisition. For example, after the accomplishment step 226, a further image acquisition step 228 is provided to acquire image data which can then be used for updating the image data in the displaying step 214. This is indicated with an arrow 230 from the further image acquisition frame 228 to the frame 214. However, it must be noted that the update feature is not a necessary feature of the method as described in relation with FIG. 7, which is indicated with a line separation symbol 232, indicating that the update is a possible add-on but not an essential feature. Once the image data is updated, also the second movement direction indicators are updated in relation to the displayed image data of the object.

For example, in case of a movement of the image due to a further image acquisition of the positioning, the second movement direction indicators are arranged, e.g. positioned or amended in their content shown to the user, according to the movement of the image acquisition apparatus itself. For example, in case of a rotation or mirroring of the image acquisition arrangement, the second movement direction indicators are also rotated or mirrored to match with the new image.

The image acquisition arrangement may be configured to acquire image data in a projection or image plane, and the second movement direction indicators relate to movement in relation to the projection plane, for example, with the projection plane and/or relating to the depth of the projection plane Before referring to FIGS. 8A to 8C, some further aspects are described in the following.

In case of an interventional C-arm procedure, X-ray images may be taken from any direction. The C-arm can be moved from a projection position to the projection position by a C-arm operator under instruction of a user, for example a surgeon. The communication between the user of a C-arm operator is facilitated with the present invention by providing the user and the C-arm operator with the same and consistent orientation information related to the last acquired X-ray image as well as the orientation information being visible on the C-arm itself. Thus, position adjustments can be clearly defined by both user and C-arm operator, thus improving the general understanding of the C-arm orientation and also the communication between the user and the C-arm operator. Consequently, the time needed, or consumed so-to-speak, for the X-ray image acquisition, can thus be significantly reduced. As another advantage of the present invention, it must be noted that the invention also allows the reduction, or nearly elimination, of superfluous use of X-ray, since unnecessary X-ray image acquisitions are prevented.

In particular, in case the C-arm is operated from a lateral position with respect to the patient anatomy, which most of the times results in a necessary rotational adjustment of the X-ray images on the X-ray monitor to ensure usual interpretation of the projected anatomy by the user in an upright orientation (head-up), or also possible mirroring of the displayed image, the clear definition in which direction to move the C-arm in order to achieve a desired projection, is facilitated according to the present invention, thus improving the overall workflow during a C-arm interventional procedure.

In particular, aspects such as the rotation and/or mirroring of the image on the X-ray monitor, the hindered sight of the C-arm operator to the operation field during position adjustment, the small visible area of the operation field, for example in case the patient is completely covered with sterile drapes, and in particular also instructions of the surgeon to move the C-arm in a certain direction that can be misleading, as an instruction like "move upwards" may refer to the displayed X-ray image as well as to the C-arm itself, which can represent different adjustment directions, are greatly relieved by the present invention by the provision of a common orientation reference system for the image acquisition arrangement itself and in relation with the displayed image presented to the surgeon.

According to the present invention, the visible clarification of the X-ray image orientation on the X-ray monitor and the according directions on the C-arm itself, or the respective input or control device like a joystick, saves time and reduces the amount of superfluously acquired X-ray images.

The present invention is feasible, for example, for mobile C-arms in particular, which are operated from the back of the system for position adjustments, which hinders the view to the operation field for the C-arm operator and therefore especially lack of visible orientation information on the C-arm in relation to the acquired mostly rotated X-ray projections on the X-ray monitor. Thus, according to the present invention, misunderstandings between user and C-arm operator are prevented, as well as the correct position adjustment of the C-arm is ensured.

According to a further aspect of the present invention, it is also provided to present orientation symbols, or in other words first movement direction indicators, on several locations on a C-arm, for example, to ensure that at least a part of one of the respective sets of symbols is visible to the user. In case the detector shows the first movement direction indicators, it is also possible to provide a sterile coverage with clear drapes to ensure the visibility of the system during surgical or interventional procedures.

Of course, it is possible to provide different types and different numbers of first and second movement direction indicators. For example, in case flat detectors with a rectangular shape are used, and thus having four visible sidewalls of a housing, these can be equipped with a respective number of symbols marking the respective directions. In case of cylindrical image intensifiers, also three, or four, five, etc., of the first and second movement direction indicators could be provided. Of course, in case the system is equipped with a reduced number of movement possibilities, the movement direction indicators are adapted accordingly in their numbers and also in their content with respect to the bijective decoding aspect.

As shown in FIG. 8A, an X-ray image 180 showing a spinal structure 182 in horizontal manner is shown on a display 184. The X-ray image 180 is provided by a C-arm device which is only partly shown in FIGS. 8A to 8C. However, a detector 186 is shown which is provided with first movement direction indicators 188, showing "12 h" and "3 h", thus relating to clock positions as described in relation with FIG. 6D.

Next to the X-ray image 180, respective second movement direction indicators 190 are provided, which second movement direction indicators are provided such that the respective movement direction in relation to the image content shown in the X-ray image 180 has the same correlation as the respective movement indicator on the detector with respect to the object, for example the patient, under investigation. In other words, the detector having the "12 o'clock" symbol 12 h on the side facing towards the head of the patient, as indicated with reference numeral 192, is also presented next to the spinal structure indicating the same direction.

As shown in FIG. 8B, for a better understanding of the image content shown, the X-ray image 180 is usually rotated such that the respective direction "12 o'clock" of the spinal structure is arranged so-to-speak with the head-up of the patient. If the surgeon is now studying the image content and wishes to have an X-ray image from an area of the spinal structure closer to the neck, i.e. in relation with a patient to move the image a bit more upwards, he or she can simply give a command to have an X-ray image from a position after a movement in the "12 o'clock" direction. The C-arch operator can then move the C-arch in a respective direction by simply manually moving the X-ray apparatus in a respective direction, which is the direction visible to a person standing on the opposite side of the surgeon in case of FIGS. 8A to 8C, or to enter a respective command, as described before.

In case the surgeon wishes to have an X-ray image from a position further down the spinal structure, he or she simply has to say "move to 6 o'clock". Despite the 6 o'clock symbol not being visible to a person standing on the other side, due to the bijective identification, the operator for moving the C-arch knows that the 6 o'clock is opposite to the 12 o'clock, thus facilitating the interaction as required.

Similar is the case, for example, if the surgeon wishes to receive information on the side of the image indicated with the 9 o'clock information. He or she can then give the movement direction "more to 9 o'clock" in order to make the C-arm operator move the C-arm respectively and to acquire a further image as shown in FIG. 8C, in which the spinal structure, here indicated with reference numeral 194, a bit more to the right side with reference to the display area.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical imaging apparatus comprising:
    an X-ray imaging device including an X-ray source and an X-ray detector, wherein the X-ray imaging device is positionable in relation to an imaged object to acquire image data of the imaged object from different directions;
    first movement direction indicators configured to indicate possible movement directions of the X-ray imaging device in relation to the imaged object, wherein a housing of the X-ray detector includes four sidewalls and one of the first movement direction indicators is provided on each of the four sidewalls of the housing of the X-ray detector; and
    a display device configured to display the image data of the imaged object and second movement direction indicators in relation to the displayed image data, wherein the second movement direction indicators indicate the possible movement directions of the X-ray imaging device in relation to the imaged object,
    wherein the second movement direction indicators correspond to the first movement direction indicators, thereby forming an orientation reference system for positioning the X-ray imaging device in relation to the imaged object.

2. The medical imaging apparatus according to claim 1, wherein the first movement direction indicators are configured such that complementary directions indicated by the first movement direction indicators and second movement direction indicators are bijectively related.

3. The medical imaging apparatus according to claim 1, wherein the first movement direction indicators include one or more of numeral indicators of "3", "6", "9", and "12" that are positioned on the four sidewalls of the housing of the X-ray detector.

4. The medical imaging apparatus according to claim 1, wherein the first movement direction indicators are provided as at least one of clock positions, cardinal directions, or colors on a chromatic circle.

5. The medical imaging apparatus according to claim 1, wherein the first movement direction indicators are configured to indicate spatial movement in relation to an image plane.

6. The medical imaging apparatus according to claim 5, wherein the display device is further configured to display indicators indicative of depth relative to the image plane.

7. The medical imaging apparatus according to claim 1, wherein the first movement direction indicators are configured as denominated symbols such that the movement directions are addressable with unambiguous messages.

8. A method for positioning an X-ray imaging device, the method comprising:
    providing first movement direction indicators configured to indicate possible movement directions of an X-ray imaging device in relation to an imaged object, wherein a housing of an X-ray detector of the X-ray imaging device includes four sidewalls and one of the first movement direction indicators is provided on each of the four sidewalls of the housing of the X-ray detector; and
    displaying the image data of the imaged object and second movement direction indicators in relation to the displayed image data, wherein the second movement direction indicators indicate the possible movement directions of the X-ray imaging device in relation to the imaged object, wherein the second movement direction indicators correspond to the first movement direction indicators, thereby forming an orientation reference system for positioning the X-ray imaging device in relation to the imaged object.

9. The method according to claim 8, wherein the first movement direction indicators include one or more of numeral indicators of "3", "6", "9", and "12" that are positioned on the four sidewalls of the housing of the X-ray detector.

10. The method according to claim 8, wherein the first movement direction indicators are provided as at least one of clock positions, cardinal directions, or colors on a chromatic circle.

11. The method according to claim 8, wherein the first movement direction indicators are configured to indicate spatial movement in relation to an image plane.

12. The method according to claim 11, wherein the display device is further configured to display indicators indicative of depth relative to the image plane.

13. A medical imaging system for positioning an X-ray imaging device, the system comprising:

first movement direction indicators configured to indicate possible movement directions of an X-ray imaging device in relation to the imaged object, wherein a housing of an X-ray detector of the X-ray imaging device includes four sidewalls and one of the first movement direction indicators is provided on each of the four sidewalls of the housing of the X-ray detector; and second movement direction indicators displayed in relation to the image data on a display device, wherein the second movement direction indicators indicate the possible movement directions of the X-ray imaging device in relation to the imaged object, wherein the second movement direction indicators correspond to the first movement direction indicators, thereby forming an orientation reference system for positioning the X-ray imaging device in relation to the imaged object.

14. The system according to claim 13, wherein the first movement direction indicators include one or more of numeral indicators of "3", "6", "9", and "12" that are positioned on the four sidewalls of the housing of the X-ray detector.

15. The system according to claim 13, wherein the first movement direction indicators are provided as at least one of clock positions, cardinal directions, or colors on a chromatic circle.

16. The system according to claim 13, wherein the first movement direction indicators are configured to indicate spatial movement in relation to an image plane.

17. The system according to claim 16, wherein the display device is further configured to display indicators indicative of depth relative to the image plane.

* * * * *